US006489459B1

(12) United States Patent
Greenwald et al.

(10) Patent No.: US 6,489,459 B1
(45) Date of Patent: *Dec. 3, 2002

(54) IDENTIFICATION OH HOP-1 AND USES THEREOF

(75) Inventors: Iva Greenwald; Xiajun Li, both of New York, NY (US)

(73) Assignee: The Trustees of Columbia University in the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/937,834

(22) Filed: Sep. 25, 1997

(51) Int. Cl.$^7$ ......................... C07H 21/02; C07H 21/04; C12N 5/10; C12N 15/63
(52) U.S. Cl. ................... 536/23.5; 435/320.1; 435/325; 536/24.1
(58) Field of Search .............................. 536/23.5, 24.1; 435/325, 320.1

(56) References Cited

PUBLICATIONS

Wilson et al., *Nature*, vol. 368, pp.32–38, 1994.*
Gellissen et al., *Bitech. Ido.*, vol. 10, pp. 179–189, 1992.*
Daigle, Isabelle, et al., Appl–1, a Caenorhabditis elegans gene encoding a protein related to the human beta–amyloid protein precursor, Proceedings of the National Academy of Sciences of the United States, vol. 90, No. 24, pp. 12045–12049, 1993 (Exhibit 1).
Levitan, D. and Greenwald, I., "Caenorhabditis elegans membrane protein, (sel–12) mRNA", EMBL Database Online, Abstract, Accession No. U35660, Sep. 29, 1995 (Exhibit 2).
Rogaev, E. I., et al., "Familial Alzheimer's Disease In Kindreds With Missense Mutations In A Gene On Chromosome 1 Related To The Alzheimer's Disease Type 3 Gene", Nature MacMillan Journals Ltd., London, GB, vol. 376, Aug. 31, 1995 pp. 775–778 (Exhibit 3).
Sherrington, R. et al., "Cloning Of A Gene Bearing Missense Mutations In Early–Onset Familial Alzheimer's Disease", Nature, GB MacMillan Journals Ltd. London, vol. 375, pp. 754–760, Jun. 29, 1995 (Exhibit 4).

* cited by examiner

*Primary Examiner*—Gary L. Kunz
*Assistant Examiner*—Stephen Gucker
(74) *Attorney, Agent, or Firm*—John P. White; Cooper & Dunham LLP

(57) ABSTRACT

This invention provides an isolated nucleic acid molecule which encodes a wildtype or mutated HOP-1. This invention also provides a purified wild-type HOP-1 protein or a purified mutated HOP-1 protein. This invention also provides a method for production of an antibody capable of binding to wild-type HOP-1 or mutated HOP-1 protein. This invention also provides an antibody capable of specifically binding to wild-type HOP-1 or mutated HOP-1. This invention also provides a transgenic animal comprising the isolated nucleic molecule encoding HOP-This invention also provides *Caenorhabditis elegans* mutants in the endogenous hop-1 gene and various method to produce such mutants. This invention also provides a method for identifying a compound which is capable of ameliorating Alzheimer's disease. This invention also provides a method for determining whether a compound is capable of ameliorating Alzheimer's disease. This invention also provides a method for producing suppressors of a hop-1 allele. This invention also provides a pharmaceutical composition effective in ameliorating Alzheimer's disease and methods of using such a pharmaceutical composition.

7 Claims, 6 Drawing Sheets

FIGURE 1A

```
HOP-1   ..........  ..........  ..........  ..........  ..........
SEL-12  ..........  ..........  .MTELPAPLS  YFQNAQMSED  NHLSNTNDNR
PS1     ..........  ..........  .MTELPAPLS  YFQNAQMSED  NHLSNTNDNR
PS2     MLTFMASDSE  EEVCDERTSL  MSAESPTPRS  CQEGRQGPED  G.........

HOP-1   ..........  ..........  ..........  ..........  MPRTKRVYSG
SEL-12  ...MPSTRRQ  QEGGGADAET  HTVYGTNLIT  NRNSQEDENV  VEEAELKYGA
PS1     ERQEHNDRRS  LGHPEPLSNG  RPQGNSRQVV  EQDEEED...  .EELTLKYGA
PS2     ..ENTAQWRS  QENEEDGEED  PDRYVCSGVP  GRPPGLE...  .EELTLKYGA

----------1----------
HOP-1   KTITGVLYPV  AICMLFVAIN  VK.LSQPEQQ  EQSKVVYGLF  HSYDTA....
SEL-12  SHVIHLFVPV  SLCMALVVFT  MNTITFYSQN  NGRHLLYTPF  VRETDSIVEK
PS1     KHVIMLFVPV  TLCMVVVVAT  IKSVSFYTRK  DG.QLIYTPF  TEDTETVGQR
PS2     KHVIMLFVPV  TLCMIVVVAT  IKSVRFYTEK  NG.QLIYTPF  TEDTPSVGQR

----------2--------------         ----------3----
HOP-1   ..DSGTITLY  LIGFLILTTS  LGVFCYQMKF  YKAIKVYVLA  NSIGILLVYS
SEL-12  GLMSLGNALV  MLCVVVLMTV  LLIVFYKYKF  YKLIHGWLIV  SSFLLLFLFT
PS1     ALHSILNAAI  MISVIVVMTI  LLVVLYKYRC  YKVIHAWLII  SSLLLLFFFS
PS2     LLNSVLNTLI  MISVIVVMTI  FLVVLYKYRC  YKFIHGWLIM  SSLMLLFLFT

----                  --------------4----------
HOP-1   VFHFQRIAEA  QSIPVSVPTF  FFLILQFGGL  GITCLHWKSH  RRLHQFYLIM
SEL-12  TIYVQEVLKS  FDVSPSALLV  LFGLGNYGVL  GMMCIHWKGP  LRLQQFYLIT
PS1     FIYLGEVFKT  YNVAVDYITV  ALLIWNLGVV  GMISIHWKGP  LRLQQAYLIM
PS2     YIYLGEVLKT  YNVAMDYPTL  LLTVWNFGAV  GMVCIHWKGP  LVLQQAYLIM

--5--         ----------6----------
HOP-1   LAGLTAIFIL  NILPDWTVWM  ALTAISFWDI  VAVLTPCGPL  KMLVETANRR
SEL-12  MSALMALVFI  KYLPEWTVWF  VLFVISVWDL  VAVLTPKGPL  RYLVETAQER
PS1     ISALMALVFI  KYLPEWTAWL  ILAVISVYDL  VAVLCPKGPL  RMLVETAQER
PS2     ISALMALVFI  KYLPEWSAWV  ILGAISVYDL  VAVLCPKGPL  RMLVETAQER

^^^^^^^^^^^^^^^^^^^^
HOP-1   GDDKFPAILY  NSS.......  ....SYVNEV  DSPDTTRSNS  TPLTEFNNSS
SEL-12  NEPIFPALIY  SSGVIYPYVL  VTAVENTTDP  REPTSSDSNT  STAFPGEASC
PS1     NETLFPALIY  SSTMVWLVNM  ..........A EGDPEAQRRV  SKNSKYNAE.
PS2     NEPIFPALIY  SSAMVWTVGM  ..........A KLDPSSQ..G  ALQLPYDPE.

HOP-1   SSRLLESDSL  ..........  ..........  ..........  .LRPPVIPRQ
SEL-12  SSETPKRPKV  KRIPQKVQIE  SNTTASTTQN  SGVRVERELA  AERPTVQDAN
PS1     STERESQDTV  AENDDGGFSE  EWEAQRDSHL  GPHRSTPESR  AAVQELSSSI
PS2     MEE....DSY  DSFGEPSYPE  VFEPPLTGYP  G.........  ...EEL....

----------7----------         ----------8--
HOP-1   IREVREVEGT  IRLGMGDFVF  YSLMLGNTVQ  TCP..LPTVV  ACFVSNLVGL
SEL-12  FHRHEEEERG  VKLGLGDFIF  YSVLLGKASS  YF..DWNTTI  ACYVAILIGL
PS1     LAGEDPEERG  VKLGLGDFIF  YSVLVGKASA  TASGDWNTTI  ACFVAILIGL
PS2     ...EEEEERG  VKLGLGDFIF  YSVLVGKAAA  TGSGDWNTTL  ACFVAILIGL

----------                    ..........
HOP-1   TITLPIVTLS  QTALPALPFP  LAIAAILYFS  SHIALTPFTD  LCTSQLILI
SEL-12  CFTLVLLAVF  KRALPALPIS  IFSGLIFYFC  TRWIITPFVT  QVSQKCLLY
PS1     CLTLLLLAIF  KKALPALPIS  ITFGLVFYFA  TDYLVQPFMD  QLAFHQFYI
PS2     CLTLLLLAVF  KKALPALPIS  ITFGLIFYFS  TDNLVRPFMD  TLASHQLYI
```

FIGURE 1B

|        | SEL-12 | PS1  | PS2  | HOP-1 |
|--------|--------|------|------|-------|
| SEL-12 | 100    | 50.7 | 54.5 | 35.4  |
| PS1    |        | 100  | 69.7 | 33.3  |
| PS2    |        |      | 100  | 32.7  |
| HOP-1  |        |      |      | 100   |

FIGURE 3A
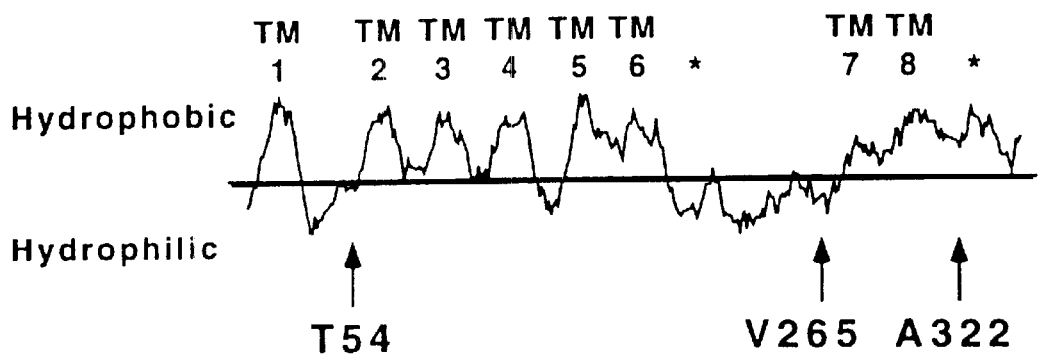
FIGURE 3B
Number of Lines Staining/Total
|         |       |     |     |
|---------|-------|-----|-----|
| LacZ    | 0/6   | 3/6 | 5/8 |
| TM::LacZ| 6/6   | 0/5 | 0/6 |
FIGURE 3C
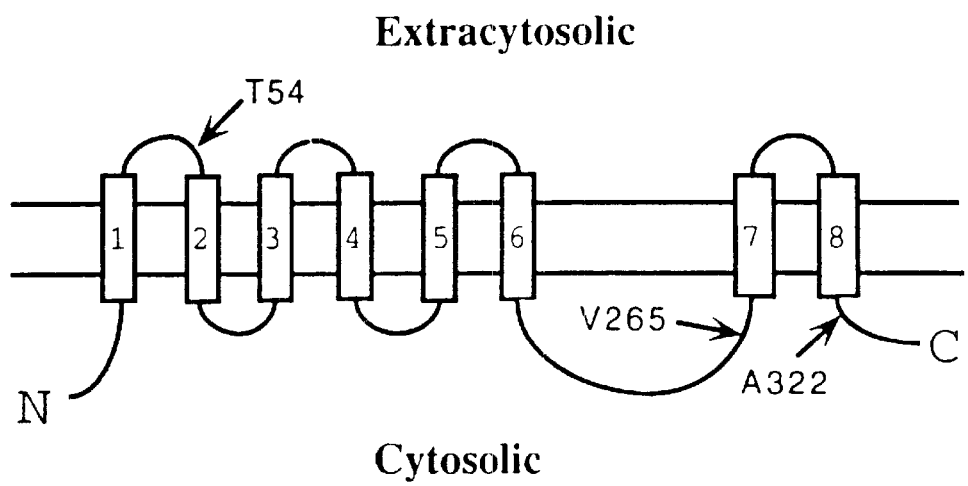

sel-12(ar131)

sel-12(ar131) +hop-1 RNA

FIGURE 5

```
         10         20         30         40         50         60
   1 ATGCCAAGAA CAAAAGAGT GTACTCCGGG AAAACCATAA CAGGAGAGTCT CTATCCTGTT   60
  61 GCAATTGCA TCTTGTTCGT CGCGATAAAT GTGAAACTCA GCCAGCCAGA ACAACAAGAA  120
 121 CAATCTAAAG TAGTATACGG ACTGTTCCAT TCATACGATA CCCGCGGATAG CGGGACAATC  180
 181 ACTTTGTATT TGATTGGATT TTTGATTTTG ACGACTAGTT TGGGAGTTT TTGTTATCAG  240
 241 ATGAAGTTTT ATAAGGCCAT AAAAGTATAC GTATTAGCCA ACAGCATTGG AATTCTGCTG  300
 301 GTTTACTCAG TTTTCCATTT CCAAAGAATA GCTGAAGCCC AATCAATTCC AGTATCTGTA  360
 361 CCAACATTTT TCTTCCTTAT TCTCCAATTC GGTGGTCTTG GAATAACATG TCTCCACTGG  420
 421 AAATCCCATC GACGACTTCA TCAATTTTAT CTTATTATGC TGCAGTCT AACTGCAATT  480
 481 TTTATTCTCA ATATTCTTCC CGACTGGACT GTTTGGATGG CATTAACAGC GATTTCATTT  540
 541 TGGGATATTG TTGCTGTTCT GACACCGTGT GGACCATTAA AAATGCTCGT GGAAACTCCG  600
 601 AATCGAGCG GAGACGACAA ATTTCCAGCT ATTTATATACA ATTCAAGTTC ATACGTGAAT  660
 661 GAAGTTGATT CCCCTGACAC AACAGGATCA AACAGTACCC CGCTAACTGA ATTCCCAGA  720
 721 TCATCGAGTT CAAGGCTTTT GGAATCTGAT TCACTTTTGA GGCCTCCAGT GATTCCAGA  780
 781 CAGATTAGAG AAGTACGAGA AGTTGAAGGA ACAATTCGGT TAGGAATCGG AGATTTGTA  840
 841 TTTATTCAC TGATGTTGGG AAATACTGTT CAAACGTGCC CACTTCCAAC TGTCGTCGCG  900
 901 TGCTTCGTAT CCAATCTGT TGGTTTGACA ATTACTCTGC CAATTGTCAC ATTATTCAA  960
 961 ACTGCACTTC CAGCATTGCC GTTCCCGTTG GCAATTGCAG CAATATCTA CTTCCTCC  1020
1021 CATATCCCAT TAACCCCATT CACCGATCTG TCCACCTCAC AGCTAATTTT AATT        1074
         10         20         30         40         50         60
```

IDENTIFICATION OH HOP-1 AND USES THEREOF

The invention disclosed in this application was supported by the United States government, National Institute of Health grant NS35556. Accordingly, the United States government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end the specification, preceding the claims.

BACKGROUND OF THE INVENTION

Genetic linkage studies have identified a number of loci associated with familial Alzheimer's disease (1). Two of these loci encode related multipass transmembrane proteins, presenilins 1 and 2 (PS1 and PS2). Mutations in the genes encoding PS1 and PS2 loci are dominant and fully penetrant for early onset Alzheimer's disease (2, 3, 4). The presenilins are ubiquitously expressed (3, 4), and found in conjunction with intracellular membranes (5). However, the normal role of presenilins, and the mechanism by which mutant presenilins cause Alzheimer's disease, are not known.

Genetic studies in simple organisms offer a powerful approach to understanding the normal role of presenilins. The C. elegans sel-12 gene encodes a protein that displays about 50% amino acid sequence identity to PS1 and PS2 (6). The sel-12 gene was also described in the Patent Cooperation Treaty international application, PCT/US96/15727, filed Sep. 27, 1996 and U.S. Provisional Application No. 60/004,387, filed Sep. 27, 1995, the content of which have incorporated into this application by reference. Genetic analysis established that reducing or eliminating sel-12 activity causes an egg-laying defective (Egl) phenotype, and that sel-12 activity facilitates the activity of LIN-12 and GLP-1, two receptors of the LIN-12/Notch family (6). SEL-12 appears to be a bona fide presenilin, since human PS1 and PS2 can rescue the Egl phenotype of a sel-12 mutant (7). Furthermore, the membrane topology of SEL-12 and PS1 appears to be similar (8, 9, 10). In addition to the functional and structural similarities, expression studies indicate that SEL-12 and human presenilins are expressed throughout development in many different cell types (3, 4, 7).

In the original application (U.S. Provisional Application No. 60/004,387, filed Sep. 27, 1995), we stated that we would identify other C. elegans genes with sequence similar to sel-12. We have identified another candidate C. elegans presenilin based on predicted amino acid sequence by searching the genomic sequence database (11, 12). Here, we show that this gene, which we have named hop-1 [hop=homolog of presenilin], encodes a functional presenilin by demonstrating that HOP-1 can rescue the Egl defect of a sel-12 mutant. We also show that HOP-1 has characteristic features of presenilin membrane topology. Finally, we show that reducing hop-1 activity in a sel-12 mutant background results in novel phenotypes, suggesting that hop-1 and sel-12 are functionally redundant.

SUMMARY OF THE INVENTION

This invention provides an isolated nucleic acid molecule encoding a HOP-1 or a mutated HOP-1. In an embodiment, the isolated nucleic acid molecule is a DNA, cDNA, genomic DNA, synthetic DNA or RNA.

This invention further provides nucleic acid molecule of at least 15 nucleotides capable of specifically hybridizing with the sequence of a nucleic acid molecule which encodes a HOP-1 or a mutated HOP-1.

The above an isolated nucleic acid molecule may be operatively linked to a promoter of RNA transcription. This invention also provide a vector which comprises the above described isolated nucleic acid molecule.

This invention also provides a host vector system for the production of a HOP-1 which comprises the vector having the above described isolated nucleic acid molecule and a suitable host.

This invention also provides a method for producing a polypeptide (e.g. HOP-1) which comprises growing a host vector system under suitable conditions permitting production of the polypeptide and recovering the polypeptide so produced.

This invention also provides a purified wild-type HOP-1 protein or purified wild-type HOP-1 fragment thereof.

This invention further provides a purified mutated HOP-1 protein or purified mutated HOP-1 fragment thereof. Further, this invention also provides a polypeptide comprising the amino acid sequence of HOP-1, including, but limited to, fusion proteins having part of their amino acid sequence of the amino acid sequence of HOP-1.

This invention provides a method for identification of a compound which is capable of binding specifically to the wild-type HOP-1 or mutated HIP-1 comprising contacting the compound with the purified HOP-1 protein of claim 11 or purified mutated HOP-1 protein under conditions permitting specific binding of said HOP-1 protein and the compound. In an embodiment, the compound is not previously known. This invention also provides a compound identified by the above method.

This invention provides an antibody capable of specifically binding to wild-type HOP-1 or mutated HOP-1. In an embodiment, the antibody capable of specifically binding to wild-type HOP-1 or mutated HOP-1 is a monoclonal antibody.

This invention also provides a method for production of an antibody capable of specifically binding to wild-type HOP-1 or mutated HOP-1 comprising steps of: a) administering an amount of the purified protein or fragment of wild-type HOP-1 or mutated HOP-1 to a suitable animal effective to produce an antibody against wild-type HOP-1 or mutated HOP-1 protein in the animal; and b) testing the produced antibody for capability to bind wild-type HOP-1 or mutated HOP-1.

This invention also provides a method for production of an antibody capable of specifically binding to wild-type HOP-1 or mutated HOP-1 comprising steps of: a) determining conserved regions revealed by alignment of the wild-type HOP-1 or mutated HOP-1 protein sequences; b) synthesizing peptides corresponding to the revealed conserved regions; c) administering an amount of the synthesized peptides to a suitable animal effective to produce an antibody against the peptides in the animal; and d) testing the produced antibody for capability to bind wild-type HOP-1 or mutant HOP-1.

This invention also provides a method for production of an antibody capable of specifically binding to wild-type HOP-1 or mutated HOP-1 by in vitro immunization.

This invention also provides a method for production of an antibody capable of specifically binding to wild-type HOP-1 or mutated HOP-1 by in vitro immunization. Further, the antibody may be labeled.

This invention provides transgenic animal comprising the isolated nucleic molecule encoding a HOP-1 or a mutated HOP-1, specifically the transgenic animal is a *Caenorhabditis elegans*.

This invention provides a method for identifying a compound which is capable of ameliorating Alzheimer's disease comprising administering an effective amount of the compound to the above transgenic animal, alteration of the conditions of the transgenic animal indicating that the compound is capable of ameliorating Alzheimer's disease.

This invention provides a method for identifying a compound which is capable of ameliorating Alzheimer's disease comprising: a) treating *Caenorhabditis elegans* mutants having reduced, increased or altered HOP-1 activity with the compound; and b) determining whether the compound suppresses, enhances or has no effect on the phenotype of the mutants, the suppression or enhancement of the phenotype indicating the compound is capable of ameliorating Alzheimer's disease.

This invention also provides a method for identifying a compound which is capable of ameliorating Alzheimer's disease comprising: a) contacting the compound with a cell which expresses HOP-1; and b) determining whether the compound increases, decreases or has no effect on the amount of HOP-1 level or activity in the cell, the increase or decrease of HOP-1 indicating that the compound is capable of ameliorating Alzheimer's disease.

This invention provides a method for identifying a compound which is capable of ameliorating Alzheimer's disease comprising administering an effective amount of the compound to the transgenic animal expressing exogenous HOP-1 and SEL-12, alteration of the conditions of the transgenic animal indicating that the compound is capable of ameliorating Alzheimer's disease.

This invention provides a method for identifying a compound which is capable of ameliorating Alzheimer's disease comprising: a) treating *Caenorhabditis elegans* mutants having reduced, increased or altered HOP-1 and SEL-12 activity with the compound; and b) determining whether the compound suppresses, enhances or has no effect on the phenotype of the mutants, the suppression or enhancement of the phenotype indicating the compound is capable of ameliorating Alzheimer's disease.

This invention provides a method for identifying a compound which is capable of ameliorating Alzheimer's disease comprising: a) contacting the compound with a cell which expresses both HOP-1 and SEL-12; and b) determining whether the compound increases, decreases or has no effect on the amount of SEL-12 level or activity or HOP-1 level or activity in the cell, the increase or decrease of SEL-12 or HOP-1 indicating that the compound is capable of ameliorating Alzheimer's disease.

This invention also provides a method for identifying a compound which is capable of ameliorating Alzheimer's disease comprising administering an effective amount of the compound to the transgenic animal which expresses exogenous HOP-1 and LIN-12, alteration of the conditions of the transgenic animal indicating that the compound is capable of ameliorating Alzheimer's disease.

This invention provides a method for identifying a compound which is capable of ameliorating Alzheimer's disease comprising: a) treating *Caenorhabditis elegans* mutants having reduced, increased or altered HOP-1 and LIN-12 activity with the compound; and b) determining whether the compound suppresses, enhances or has no effect on the phenotype of the mutants, the suppression or enhancement of the phenotype indicating the compound is capable of ameliorating Alzheimer's disease.

This invention provides method for identifying a compound which is capable of ameliorating Alzheimer's disease comprising: a) contacting the compound with a cell which expresses both HOP-1 and LIN-12; and b) determining whether the compound increases, decreases or has no effect on the amount of LIN-12 level or activity or HOP-1 level or activity in the cell, the increase or decrease of LIN-12 or HOP-1 indicating that the compound is capable of ameliorating Alzheimer's disease.

This invention provides a method for producing suppressors of a hop-1 allele comprising: a) mutagenizing hop-1; sel-12 mutant hermaphrodites with an effective amount of a mutagen; b) screening for revertants in the F1, F2, and F3 generations; and c) isolating the screened revertants. This invention also provides for a suppressor identified by the above-described method.

This invention provides a method for identifying a suppressor gene comprising performing DNA sequence analysis of the above suppressor to identify the suppressor gene. This invention also provides an enhancer identified by the above-described method.

This invention provides a method for producing enhancers of a hop-1 allele comprising: a) mutagenizing hop-1 mutant hermaphrodites with an effective amount of a mutagen; b) screening for enhanced mutants or synthetic phenotypes in the F1, F2, and F3 generations; and c) isolating the enhanced mutants. This invention also provides for a suppressor identified by the above-described method.

This invention provides a method for identifying an enhancer gene comprising performing DNA sequence analysis of the above enhancer to identify the enhancer gene. This invention also provides an enhancer identified by the above-described method.

This invention provides a pharmaceutical composition comprising an effective amount of the compound identified by the above methods and a pharmaceutically acceptable carrier.

This invention provides a method of ameliorating Alzheimer's disease which comprises administrating the above pharmaceutical composition in an amount effective to ameliorate Alzheimer's disease.

BRIEF DESCRIPTION OF THE FIGURES

FIG. 1. A. Predicted protein sequence of HOP-1 (SEQ ID NO:4) and its alignment with the predicted protein sequences of *C. elegans* SEL-12, (SEQ ID NO:5) human PS1, (SEQ ID NO:6) human PS2(SEQ ID NO:4). The Pileup program of the GCG-Wisconsin package was used to create this alignment (30). Amino acids that are identical between at least three of the four proteins are highlighted in black. The predicted transmembrane domains based on topological studies of SEL-12 (9) are overlined. Two additional features referred to in the Discussion are marked: a hydrophobic region found in SEL-12 ("the seventh hydrophobic region"), PS1 and PS2 that does not span the membrane is overlined with carets (^), and a hydrophobic region found in all four presenilins (the "tenth hydrophobic region" of SEL-12) that is not membrane spanning is overlined with dots. The sequence of SEL-12 is from (6), with a minor correction as described in (7). The PS1 sequence is from (4) and the PS2 sequence is from (3).

B. Amino acid identity among the *C. elegans* and human presenilins. The GAP program of the GCG-Wisconsin package was used to calculate the percentage of amino acid identity (30).

Figure 2:
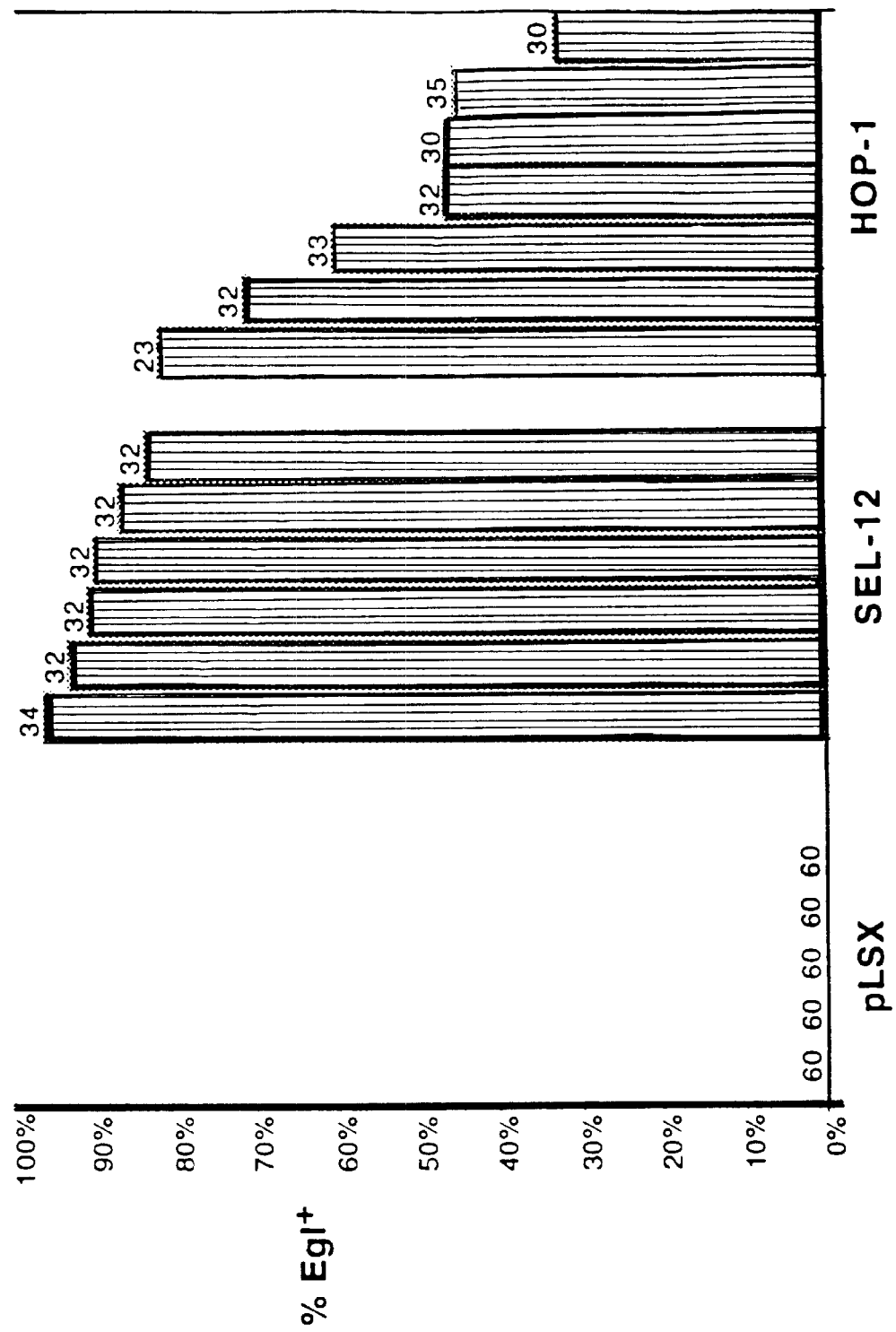
Figure 4A:
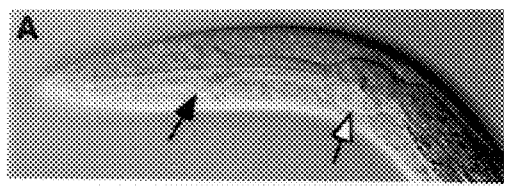
Figure 4B:
Figure 4C:
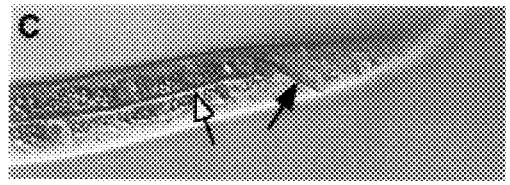
Figure 4D:
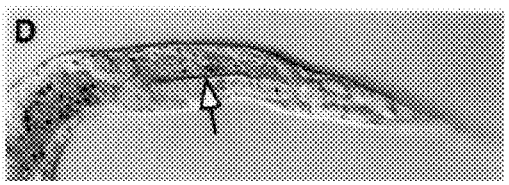
Figure 4E:
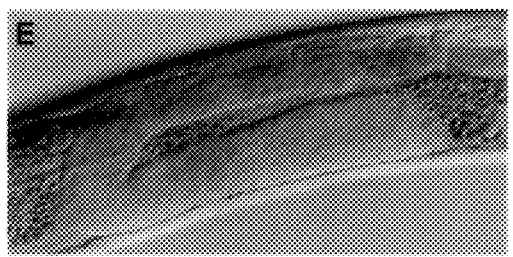
Figure 4F:

FIG. 2. Rescue of the sel-12 egg-laying defective (Egl) and abnormal vulva phenotypes by HOP-1. The data is shown for transgenic lines generated by injecting a construct that places a sel-12(+) cDNA or a hop-1(+) cDNA under the control of sel-12 5' flanking sequence at a concentration of 20 mg/ml. Each line in the histogram represents data for an independent transgenic line; the number of hermaphrodites scored is shown above each line. The transgene is indicated on the horizontal axis. The percentage of Egl+ hermaphrodites is indicated on the vertical axis. For pLSX control lines, Egl+ hermaphrodites were never seen. See Materials and Methods for details about generating and scoring transgenic lines.

FIG. 3. HOP-1 topology.

A. Hydrophobicity plot of HOP-1, generated using the Kyte-Doolittle algorithm (31) (window size=15). Transmembrane domains based on topological studies of SEL-12 (9) are numbered. The location of hydrophobic regions of SEL-12 that do not span the membrane are indicated by asterisks. Arrows indicate the position of LacZ and TM::LacZ fusions.

B. β-galactosidase activity of HOP-1::LacZ and HOP-1::TM::LacZ fusion proteins.

C. Inferred topology of HOP-1, based on the data in B and sequence similarities with other presenilins.

FIG. 4. Nomarski photomicrographs of sel-12(ar131) hermaphrodites. Panels A, C and E show sel-12(ar131) hermaphrodites, and panels B, D and F show progeny of sel-12(ar131) hermaphrodites that were injected with hop-1antisense RNA (see Materials and Methods).

(A,B) The head region. The white arrow indicates the position of the posterior bulb; the black arrow indicates the position of the anterior bulb of the pharynx, which is often missing in progeny of hop-1 RNA-injected parents, as in glp-1 mutants (25, 26).

(C,D) The tail region. The white arrow indicates the intestine; the black arrow indicates the rectum, which is often missing in progeny of hop-1 RNA-injected parents, as in lin-12 glp-1 double mutants (27).

(E,F) The gonad of L4 hermaphrodites. In F, germline proliferation is reduced, and the arrow indicates a region of the germline undergoing premature spermatogenesis; these phenotypes are characteristic of glp-1mutants (25, 26).

FIG. 5 cDNA sequence of HOP-1 from C. elegans (SEQ ID NO:8)

DETAILED DESCRIPTION OF THE INVENTION

Throughout this application, references to specific nucleotides are to nucleotides present on the coding strand of the nucleic acid. The following standard abbreviations are used throughout the specification to indicate specific nucleotides:

| C = cytosine | A = adenosine |
|---|---|
| T = thymidine | G = guanosine |

A "gene" means a nucleic acid molecule, the sequence of which includes all the information required for the normal regulated production of a particular protein, including the structural coding sequence, promoters and enhancers. A gene is also a functional unit defined by mutation.

The nucleic acids or oligonucleotides of the subject invention also include nucleic acids or oligonucleotides coding for polypeptide analogs, fragments or derivatives which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These nucleic acids or oligonucleotides include: the incorporation of codons "preferred" for expression by selected non-mammalian or mammalian hosts; the provision of sites for cleavage by restriction endonuclease enzymes; and the provision of additional initial, terminal or intermediate DNA sequences that facilitate construction of readily expressed vectors.

The nucleic acids and oligonucleotides described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

This invention provides an isolated nucleic acid molecule encoding a HOP-1 or a mutated HOP-1. In an embodiment, the isolated nucleic acid molecule is a DNA, cDNA, genomic DNA, synthetic DNA or RNA.

The invention provides an isolated nucleic acid molecule encoding HOP-1, wherein the encoded HOP-1 has substantially the same amino acid sequence as shown in FIG. 1.

As used in this application, "HOP-1" means and includes any polypeptide having HOP-1 activity. Thus, this term includes any such polypeptide whether naturally occurring and obtained by purification from natural sources or non-naturally occuring and obtained synthetically, e.g. by recombinant DNA procedures. Moreover, the term includes any such polypeptide whether its sequence is substantially the same as, or identical to the sequence of any mammalian homolog of the C. elegans polypeptide, e.g. murine, bovine, porcine, etc. homologs.

As used in this application, hop-1 means and includes the C. elegans gene defined by mutation that encodes a protein having HOP-1 activity. One example of such gene is shown in FIG. 5. It also includes such genes in other other organisms, such as Drosophila, mouse, and human.

The nucleic acid of the subject invention also include nucleic acids that encode for polypeptide analogs, fragments or derivatives which differ from naturally-occurring forms in terms of the identity or location of one or more amino acid residues (including deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all properties of the naturally-occuring forms.

The polypeptide of the subject invention also includes analogs, fragments or derivatives which differ from naturally-occurring forms.

This invention further provides nucleic acid molecule of at least 15 nucleotides capable of specifically hybridizing with the sequence of a nucleic acid molecule which encodes a HOP-1 or a mutated HOP-1. In an embodiment, the nucleic acid molecule is DNA or RNA.

These oligonucleotides may be DNA or RNA. Such oligonucleotides may be used in accordance with well known standard methods for known purposes, for example, to detect the presence in a sample of DNA which will hybridize thereto.

As used herein, "capable of specifically hybridizing" means wherein the oligonucleotide will selectively bind to only sequences which are unique to either nucleic acids encoding wildtype or mutant HOP-1.

The oligonucleotides include, but are not limited to, oligonucleotides that hybridize to mRNA encoding HOP-1 so as to prevent translation of the protein or cause RNA-mediated interference of endogenous gene expression.

This invention also provides a nucleic acid having a sequence complementary to the sequence of the isolated nucleic acid which encodes HOP-1.

The above isolated nucleic acid molecule may be operatively linked to a promoter of RNA transcription. This invention also provide a vector which comprises the above described isolated nucleic acid molecule. In an embodiment, the vector is a plasmid. Further other numerous vector backbones known in the art as useful for expressing proteins may be employed. Such vectors include but are not limited to: adenovirus, simian virus 40 (SV40), cytomegalovirus (CMV), mouse mammary tumor virus (MMTV), Moloney murine leukemia virus, murine sarcoma virus, and Rous sarcoma virus, DNA delivery systems, i.e liposomes, and expression plasmid delivery systems.

This invention also provides a host vector system for the production of a HOP-1 which comprises the vector having the above described isolated nucleic acid molecule and a suitable host. Suitable host includes a cell which includes, but is not limited to, prokaryotic or eukaryotic cells, e.g. bacterial cells (including gram positive cells), yeast cells, fungal cells, insect cells and animal cells.

Suitable animal cells include, but are not limited to, HeLa cells, Cos cells, CV1 cells and various primary mammalian cells. Numerous mammalian cells may be used as hosts, including, but not limited to, the mouse fibroblast cell NIH 3T3, CHO cells, Ltk⁻ cells, etc. Expression plasmids such as that described supra may be used to transfect mammalian cells by methods well known in the art such as calcium phosphate precipitation, electroporation.

This invention also provides a method for producing a polypeptide (e.g. HOP-1) which comprises growing a host vector system under suitable conditions permitting production of the polypeptide and recovering the polypeptide so produced. Methods of recovering polypeptides produced in such host vector systems are well-known in the art and typically include steps involving cell lysis, solubilization and chromatography. This invention also provides a method of obtaining a polypeptide in purified form which comprises: (a) introducing a vector, as described above, into a suitable host cell; (b) culturing the resulting cell so as to produce the polypeptide; (c) recovering the polypeptide produced in step (b); and (d) purifying the polypeptide so recovered. As discussed above the vector may include a plasmid, cosmid, yeast artificial chromosome, bacteriophage or eukaryotic viral DNA. Also, the host cell may be a bacterial cell (including gram positive cells), yeast cell, fungal cell, insect cell or animal cell. Suitable animals cells include, but are not limited to HeLa cells, Cos Cells, CV1 cells and various primary mammalian cells. Culturing methods useful for permitting transformed or transfected host cells to produce polypeptides are well known in the art as are the methods for recovering polypeptides from such cells and for purifying them.

This invention also provides a purified wild-type HOP-1 protein or purified wild-type HOP-1 fragment thereof. This invention further provides a purified mutated HOP-1 protein or purified mutated HOP-1 fragment thereof. Further, this invention also provides a polypeptide comprising the amino acid sequence of HOP-1, including, but not limited to, fusion proteins having part of their amino acid sequence of the amino acid sequence of HOP-1.

Further, this invention provides where the HOP-1 produced is labeled. Different types of labeling exist. The labeling may be by various means. For instance one may tag the produced polypeptide with an established epitope such as myc. As discussed later in this application, such means of labeling are well known in the art. Further, one could also use other types of labels such as fluorescent, bioluminescent and metals.

This invention provides a method for identification of a compound which is capable of binding specifically to the wild-type HOP-1 or mutated HIP-1 comprising contacting the compound with the purified HOP-1 protein or purified mutated HOP-1 protein under conditions permitting specific binding of said HOP-1 protein and the compound.

In an embodiment, the compound is not previously known. This invention also provides a compound identified by the abvoe method.

This invention provides an antibody capable of specifically binding to wild-type HOP-1 or mutated HOP-1.

In an embodiment, the antibody capable of specifically binding to wild-type HOP-1 or mutated HOP-1 is a monoclonal antibody.

Antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

This invention also provides a method for production of an antibody capable of specifically binding to wild-type HOP-1 or mutated HOP-1 comprising steps of: a) administering an amount of the purified protein or fragment of wild-type HOP-1 or mutated HOP-1 to a suitable animal effective to produce an antibody against wild-type HOP-1 or mutated HOP-1 protein in the animal; and b) testing the produced antibody for capability to bind wild-type HOP-1 or mutated HOP-1.

This invention also provides a method for production of an antibody capable of specifically binding to wild-type HOP-1 or mutated HOP-1 comprising steps of: a) determining conserved regions revealed by alignment of the wild-type HOP-1 or mutated HOP-1 protein sequences; b) synthesizing peptides corresponding to the revealed conserved regions; c) administering an amount of the synthesized peptides to a suitable animal effective to produce an antibody against the peptides in the animal; and d) testing the produced antibody for capability to bind wild-type HOP-1 or mutant HOP-1.

This invention also provides a method for production of an antibody capable of specifically binding to wild-type HOP-1 or mutated HOP-1 by in vitro immunization.

In an embodiment, the produced antibody is tested by Western blot analysis, immunoprecipitation or staining of cells or tissue sections.

This invention also provides a method for production of an antibody capable of specifically binding to wild-type HOP-1 or mutated HOP-1 by in vitro immunization. Further, the antibody may be labeled.

The labeled antibody may be a polyclonal or monoclonal antibody. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. The detectable marker may be, for example, radioactive or fluorescent. Methods of labeling antibodies are well known in the art.

This invention provides transgenic animal comprising the isolated nucleic molecule encoding a HOP-1 or a mutated HOP-1, specifically the transgenic animal is a *Caenorhabditis elegans*.

This invention also provides *Caenorhabditis elegans* mutants in the endogenous hop-1 gene.

This invention further provides *Caenorhabditis elegans* mutants in the endogenous hop-1 gene generated as synthetic lethal mutations with sel-12, comprising: a) mutagenizing appropriately marked sel-12 mutants; b) screening for mutations that are lethal in the presence of a sel-12 mutation; and c) demonstrating that such synthetic lethal mutations are alleles of hop-1 by DNA analysis.

This invention also provides *Caenorhabditis elegans* mutants in the endogenous hop-1 gene generated by screening for deletions in the endogenous gene using the polymerase chain reaction.

This invention provides a method for identifying a compound which is capable of ameliorating Alzheimer's disease comprising administering an effective amount of the compound to the above transgenic animal, alteration of the conditions of the transgenic animal indicating that the compound is capable of ameliorating Alzheimer's disease.

This invention provides a method for identifying a compound which is capable of ameliorating Alzheimer's disease comprising: a) treating *Caenorhabditis elegans* mutants having reduced, increased or altered HOP-1 activity with the compound; and b) determining whether the compound suppresses, enhances or has no effect on the phenotype of the mutants, the suppression or enhancement of the phenotype indicating the compound is capable of ameliorating Alzheimer's disease.

This invention also provides a method for identifying a compound which is capable of ameliorating Alzheimer's disease comprising: a) contacting the compound with a cell which expresses HOP-1; and b) determining whether the compound increases, decreases or has no effect on the amount of HOP-1 level or activity in the cell, the increase or decrease of HOP-1 indicating that the compound is capable of ameliorating Alzheimer's disease.

This invention provides a method for identifying a compound which is capable of ameliorating Alzheimer's disease comprising administering an effective amount of the compound to the transgenic animal expressing exogenous HOP-1 and SEL-12, alteration of the conditions of the transgenic animal indicating that the compound is capable of ameliorating Alzheimer's disease.

This invention provides a method for identifying a compound which is capable of ameliorating Alzheimer's disease comprising: a) treating *Caenorhabditis elegans* mutants having reduced, increased or altered HOP-1 and SEL-12 activity with the compound; and b) determining whether the compound suppresses, enhances or has no effect on the phenotype of the mutants, the suppression or enhancement of the phenotype indicating the compound is capable of ameliorating Alzheimer's disease.

This invention provides a method for identifying a compound which is capable of ameliorating Alzheimer's disease comprising: a) contacting the compound with a cell which expresses both HOP-1 and SEL-12; and b) determining whether the compound increases, decreases or has no effect on the amount of SEL-12 level or activity or HOP-1 level or activity in the cell, the increase or decrease of SEL-12 or HOP-1 indicating that the compound is capable of ameliorating Alzheimer's disease.

This invention also provides a method for identifying a compound which is capable of ameliorating Alzheimer's disease comprising administering an effective amount of the compound to the transgenic animal which expresses exogenous HOP-1 and LIN-12, alteration of the conditions of the transgenic animal indicating that the compound is capable of ameliorating Alzheimer's disease.

This invention provides a method for identifying a compound which is capable of ameliorating Alzheimer's disease comprising: a) treating *Caenorhabditis elegans* mutants having reduced, increased or altered HOP-1 and LIN-12 activity with the compound; and b) determining whether the compound suppresses, enhances or has no effect on the phenotype of the mutants, the suppression or enhancement of the phenotype indicating the compound is capable of ameliorating Alzheimer's disease.

This invention provides method for identifying a compound which is capable of ameliorating Alzheimer's disease comprising: a) contacting the compound with a cell which expresses both HOP-1 and LIN-12; and b) determining whether the compound increases, decreases or has no effect on the amount of LIN-12 level or activity or HOP-1 level or activity in the cell, the increase or decrease of LIN-12 or HOP-1 indicating that the compound is capable of ameliorating Alzheimer's disease.

This invention provides a method for producing suppressors of a hop-1 allele comprising: a) mutagenizing hop-1; sel-12 mutant hermaphrodites with an effective amount of a mutagen; b) screening for revertants in the F1, F2, and F3 generations; and c) isolating the screened revertants.

This invention also provides for a suppressor identified by the above-described method.

This invention provides a method for identifying a suppressor gene comprising performing DNA sequence analysis of the above suppressor to identify the suppressor gene.

This invention also provides an enhancer identified by the above-described method.

This invention provides a method for producing enhancers of a hop-1 allele comprising: a) mutagenizing hop-1 mutant hermaphrodites with an effective amount of a mutagen; b) screening for enhanced mutants or synthetic phenotypes in the F1, F2, and F3 generations; and c) isolating the enhanced mutants.

This invention also provides for a suppressor identified by the above-described method.

This invention provides a method for identifying an enhancer gene comprising performing DNA sequence analysis of the above enhancer to identify the enhancer gene.

This invention also provides an enhancer identified by the above-described method.

This invention provides a pharmaceutical composition comprising an effective amount of the compound identified by the above methods and a pharmaceutically acceptable carrier.

For the purposes of this invention "pharmaceutically acceptable carriers" means any of the standard pharmaceutical carriers. Examples of suitable carriers are well known in the art and may include, but not limited to, any of the standard pharmaceutical carriers such as a phosphate buffered saline solutions, phosphate buffered saline containing Polysorb 80, water, emulsions such as oil/water emulsion, and various type of wetting agents. Other carriers may also include sterile solutions, tablets, coated tablets, and capsules.

Typically such carriers contain excipients such as starch, milk, sugar, certain types of clay, gelatin, stearic acid or salts thereof, magnesium or calcium sterate, talc, vegetable fats or oils, gums, glycols, or other known excipients. Such carriers may also include flavor and color additives or other ingredients. Compositions comprising such carriers are formulated by well known conventional methods.

This invention provides a method of ameliorating Alzheimer's disease which comprises administrating the above pharmaceutical composition in an amount effective to ameliorate Alzheimer's disease.

This invention is illustrated in the Experimental Details section which follows. These sections are set forth to aid in an understanding of the invention but are not intended to, and should not be construed to, limit in any way the invention as set forth in the claims which follow thereafter.

Experimental Details

Materials and Methods

Genetic Methods.

Methods for handling and culturing C. elegans have been described by (13). The wild-type parent for all strains used was C. elegans var. Bristol strain N2 (13). Rescue and RNA-mediated interference experiments were performed at 20° C. Strains for topological analysis were grown at 25° C., a temperature that maximizes β-galactosidase activity (J. Way, personal communication).

hop-1 cDNA hop-1 cDNA was isolated by polymerase chain reactions (PCR) using a cDNA library provided by R. Barstead (14) as template. A major portion of hop-1 cDNA was amplified with primers from within the exons of Genefinder (12) predicted gene C18E3.b. The forward primer, C18LXJ1-5' CGGGATCCTTTGCATGTTGTTCGTCGCG, (SEQ ID NO:1) harbors amino acids of CysMetLeuPheValAla in the amino terminal region of C18E3.b. The reverse primer, C18LXJ2-5' CGGGATCCAAATTAGCTGTGAGGTGC, (SEQ ID NO:2) is complementary to amino acids of ThrSerGlnLeuIle in the carboxy terminal region of C18E3.b. The amplified product was subcloned and sequenced to verify the exon/intron boundary predicted by Genefinder. A small exon in the carboxy terminal region of hop-1 was missing in predicted C18E3.b.

The 5' and 3' ends of the transcript was determined using rapid amplification of cDNA ends (RACE). For 5' RACE, primers with the sequence of either spliced leader SL1 (15) or SL2 (16) were used for the amplication. A specific product was only obtained with SL1 as one of the primers after a second round of amplication using a nested primer inside the first amplification product. For 3 ' RACE, dT-adaptor, 5' GGCCACGCGTCGACTAGTACTTTTTTTTTTTTTTTTT, (SEQ ID NO:3) was used for the amplication. After a second round of amplication using a nested primer inside the first amplification product, a specific product was obtained and subcloned into pBluescript.

Full-length hop-1 cDNA was obtained by joining these three cDNA fragments with appropriate restriction endonucleases.

Plasmids

PLSX (9) is an expression vector containing 2.8 kb of sel-12 5' flanking region, a polylinker, and 755 bp of 3' noncoding region, including a polyadenylation sequence, from the unc-54 gene (17). cDNAs containing initiation codons are inserted into the polylinker site, and expression is driven by sel-12 5' flanking region. This vector leads to good expression in a subset of cells that express sel-12 (x. L., D. Levitan and I. G., unpublished observations), and served as the parent plasmid for the rescue and topology experiments. The full-length hop-1 cDNA, or portions of hop-1 cDNA fused in-frame to the cDNAs encoding LacZ or TM::LacZ proteins (17), were placed into pLSX.

Transgenic Lines

Transgenic lines were established by microinjection of plasmid mixtures into the hermaphrodite germline to create extrachromosomal arrays (18).

For the rescue experiments, pLSX::hop-1 or pLSX::sel-12 was injected at a concentration of 20 mg/ml into recipient sel-12 (ar171) unc-1 (e538) hermaphrodites along with 100 mg/ml of pRF4, a plasmid containing the cloned dominant rol-6(su1006) gene (18), as a cotransformation marker. F1 Roller progeny were picked, and F2 Roller progeny used to establish lines. To assess rescue of sel-12(ar171), approximately 30 L4 Rol progeny from 5–7 independent lines were picked individually and scored daily for the ability to lay eggs. sel-12(ar171) never lays eggs (6), and transgenic hermaphrodites were scored as "Egl$^+$" if they displayed robust egg-laying characteristic of wild-type hermaphrodites for two days as adults.

For the topology experiments, plasmids were injected at a concentration of 20 mg/ml into recipient N2 hermaphrodites along with 100 mg/ml of pRF4, a plasmid containing the cloned dominant rol-6(su1006) gene (18), as a cotransformation marker. F1 Roller progeny were picked, and F2 Roller progeny used to establish lines. Larvae were fixed using an acetone fixation protocol described by (19) and stained for β-galactosidase activity overnight at room temperature.

RNA-mediated Interference Experiments

Plasmids harboring hop-1 and sel-12 cDNAs were linearized with appropriate restriction endonucleases, and served as templates for production of antisense RNAs in vitro (Stratagene). Transcripts were treated with DNAse, followed by phenol-chloroform extractions and isopropanol precipitation. After washing once with 70% ethanol, pellets were resuspended in DEPC-treated distilled water. Wild-type (N2), sel-12(ar131) or sel-12(ar171) unc-1(e538) young adult hermaphrodites were injected with RNAs in both distal gonad arms at an estimated concentration ranging from 50 mg/ml to 250 mg/ml. Injected worms were plated individually at 20° C. and were transferred to a new plate every day. Their progeny were counted and examined under the dissecting microscope. Embryonic arrest (dead eggs) was assessed one day after the eggs were laid.

At least 12, and as many as 30, hermaphrodites were injected with antisense RNAs for each set of injections into a given recipient. The injection protocol was repeated two independent times for hop-1 or sel-12 RNA, or DEPC-dH$_2$O into wild-type N2 hermaphrodites, and two independent times for sel-12 RNA or DEPC-dH$_2$O into sel-12 mutant hermaphrodites. We did not observe novel mutant phenotypes or reduced viability of progeny in any of these experiments.

Injection of hop-1 RNA into sel-12(ar131) or sel-12 (ar171) unc-1 hermaphrodites was repeated four independent times for each mutant genotype. Offspring displaying Glp-1 and Lag phenotypes were seen in all four sets of injections into each mutant. We also often observed many inviable embryos (Emb phenotype) among the progeny of injected hermaphrodites; we do not know if this reflects the combination of reduced maternal and zygotic glp-1 and lin-12 activity, or the involvement of hop-1 in other processes. sel-12 mutant hermaphrodites injected with DEPC-dH$_2$O did not produce offspring displaying Glp-1 or Lag phenotypes, or a significant increase in the number of inviable offspring.

It is difficult to quantify precisely the different phenotypic classes obtained among the progeny of injected sel-12 Egl hermaphrodites. However, for injections into sel-12(ar131), in some experiments we quantified the proportion of mutant offspring among the progeny of injected Egl$^+$ hermaphrodites. For example, in one set of injections in which hop-1 RNA (at approximately 200 mg/ml) was injected into sel-12(ar131) hermaphrodites, we observed 56 viable adult hermaphrodites and 103 inviable offspring (65% inviable); 40/56 (71%) viable adult hermaphrodites were sterile, and all sterile hermaphrodites examined had defects characteristic of reducing glp-1 activity in the germ line. A high proportion of sterile and inviable offspring was reproducibly seen in all injections involving hop-1 RNA (data not shown).

Experimental Results

Identification and Sequence of a New Candidate Presenilin.

We searched the *C. elegans* genome sequence database (11, 12) with the SEL-12 amino acid sequence and identified a second potential presenilin gene, C18E3.b. We obtained and sequenced cDNAs for C18E3.b (Genbank accession number AF021905. The predicted protein encoded by this cDNA is also shown aligned with SEL-12, PS1 and PS2 in FIG. 1. Because the functional and structural studies described below suggest that C18E3.b is a bona fide presenilin, we have named C18E3.b hop-1, for homolog of presenilin.

hop-1 Can Rescue the Egg-laying Defect of a sel-12 Presenilin Mutant.

Human PS1 and PS2 can efficiently rescue the distinctive egg-laying defective (Egl) phenotype caused by a mutation that reduces sel-12 activity (7). We used the same basic approach to assess the presenilin activity of hop-1. The sel-12(ar171) mutation strongly reduces sel-12 activity, so that all sel-12(ar171) hermaphrodites are Egl. We created transgenes expressing hop-1 by microinjecting a plasmid containing the hop-1 cDNA under the control of 2.8 kb of sel-12 5' flanking region into sel-12(ar171) hermaphrodites (see Materials and Methods). We found that hop-1 can efficiently rescue the Egl defect of sel-12(ar171) hermaphrodites (FIG. 2), indicating that HOP-1 is a functional homolog of SEL-12, PS1 and PS2.

HOP-1 Has Similar Topology to SEL-12 Presenilin.

The amino and carboxy termini of SEL-12 and PS1 are cytosolic, as is a large intracellular loop located between the sixth and seventh transmembrane domains (8, 9). We have determined that HOP-1 has these essential features of presenilin topology using the LacZ hybrid protein approach that we used to deduce the topology of SEL-12 presenilin (9). If LacZ is fused at different points in a membrane protein, its location in the cytosol or in an extracytosolic compartment, and hence the topology of the membrane protein, can be deduced by its activity, since β-galactosidase is active within the cytosol but not in the extracytosolic compartment (20, 21).

We constructed transgenes encoding hybrid HOP-1::LacZ proteins, in which LacZ or TM::LacZ (TM denotes a short hydrophilic spacer followed by a synthetic transmembrane domain; Fire et al., 1990) was placed after the first, sixth or eighth putative transmembrane domains (see FIG. 3). Several independent transgenic *C. elegans* lines expressing individual LacZ hybrid proteins were established (18) and assayed for β-galactosidase activity (19). Transgenic lines expressing individual hybrid proteins should consistently stain positively for β-galactosidase activity if the LacZ moiety is located in the cytosol, but should not stain if LacZ is located extracytosolically; for each pair of hybrid proteins, one hybrid should be active while the other should not be active. Our results suggest that the amino terminus, loop and carboxy terminus of HOP-1 are all cytosolic (FIG. 3), as they are in other presenilins (8, 9).

Reducing hop-1 Activity Causes Novel Phenotypes In a sel-12 Mutant Background.

RNA-mediated interference is a widely used method for reducing gene activity in *C. elegans*, and has been shown in many cases to give a phenotype similar to null alleles (22, 23). Both antisense and sense RNAs appear to have the same effect (22). RNA-mediated interference appears to cause targeted suppression of the corresponding gene in the germline of injected hermaphrodites, so that progeny display phenotypes associated with loss of gene function (C. Mello, personal communication). Although the penetrance of these phenotypes is incomplete, the expressivity can be high. Maternal gene activities seem to be more sensitive to RNA-mediated interference than zygotic gene activities.

We injected the germ lines of wild-type and sel-12 mutant hermaphrodites with antisense RNA from sel-12 or hop-1 (Table 1).

Table 1. Summary of novel phenotypes obtained by RNA interference.

TABLE 1

Summary of novel phenotypes obtained by RNA interference.

| | Recipient genotype | | |
|---|---|---|---|
| RNA injected | wild-type | sel-12 (ar131) | sel-12 (ar171)[a] |
| DEPC-dH$_2$O | none | none | none |
| sel-12 | none | none | none |
| hop-1 | none | Glp-1, Lag, Emb | Glp-1, Lag, Emb |

See Materials and Methods for a detailed description of the RNA interference experiments and Results for more information about mutant phenotypes. Abbreviations: Glp-1, phenotypes associated with the reduction of glp-1 activity: defective germline proliferation and premature entry of germ cells into meiosis, or missing anterior pharynx (25, 26). Lag, phenotypes associated with the concomitant reduction of lin-12 and glp-1 activity: missing rectum and/or excretory cell (27). Emb, embryonic lethal (cellular anatomy not analyzed). DEPC-dH$_2$O, diethyl pyrocarbonate-treated distilled water. a Complete genotype: sel-12(ar171) unc-1 (e538)

When wild-type hermaphrodites were injected with sel-12 or hop-1 RNA, no mutant offspring were seen. However, when sel-12 mutant hermaphrodites were injected with hop-1 RNA, there were many dead embryos, arrested larvae, and sterile hermaphrodites among the progeny. These phenotypes are not seen in sel-12 mutants (6) or in sel-12 mutant hermaphrodites injected with sel-12 RNA or water (Table 1).

Previous work established that sel-12 facilitates lin-12 and glp-1 activity (6). Characteristic anatomical defects due to abnormal cell fate specification are observed when lin-12 or glp-1 activity is reduced; additional defects are observed when the activities of both genes are reduced concomitantly (24, 25, 26, 27). Many of these various defects were frequently observed among the progeny of sel-12 mothers that had been injected with hop-1 RNA (Table 1, FIG. 4). (1) All of the sterile hermaphrodites examined had a severely reduced number of germ cells and premature differentiation of germ cells as sperm, the hallmarks of reduced glp-1 activity in the germ line (25, 26). (2) Some arrested larvae lacked an anterior pharynx, a defect associated with reduced maternal glp-1 activity (25, 26). (3) Some arrested larvae lacked a rectum and an excretory cell, the hallmarks of the "Lag" phenotype associated with concomitantly reduced lin-12 and glp-1 activity, and to a lesser extent with reduced lin-12 activity (27).

Although many dead embryos and arrested larvae display defects known to result from reduced lin-12 and/or glp-1 activity, they may also have additional anatomical defects (data not shown). Further analysis of embryos depleted in the activities of both hop-1 and sel-12 will be facilitated by the isolation of conventional hop-1 mutations, and the construction of hop-1(−); sel-12(−) double mutants.

Experimental Discussion

Despite considerable sequence differences from other presenilins, HOP-1 appears to be a bona fide presenilin. HOP-1 can rescue the Egl defect caused by mutations in sel-12 when hop-1 is expressed under the control of sel-12 regulatory sequences. Furthermore, HOP-1 has the essential topological characteristics of the other presenilins. Finally, hop-1 and sel-12 appear to be functionally redundant. It is curious that both C. elegans and humans have at least two functional presenilins, but the meaning of this observation is unclear.

Sequence Comparison Between HOP-1 and Other Presenilins.

SEL-12, PS1 and PS2 are highly similar in all eight transmembrane domains as well as two other hydrophobic regions that do not appear to span the membrane (9). Most of the sequence divergence is found in two cytosolic regions, one at the amino terminus and the other in the loop between the sixth and seventh transmembrane domains. This region of the loop has features reminiscent of a PEST protein destabilization sequence (9). HOP-1 is similar to the other presenilins in terms of the overall length and spacing of the transmembrane domains, the presence of a PEST sequence between the sixth and seventh hydrophobic domains, and the presence of a hydrophobic region following the eighth transmembrane domain. However, HOP-1 is considerably more diverged from SEL-12, PS1 and PS2 at the primary amino acid sequence level (FIG. 1).

The divergence of HOP-1 from the other presenilins is instructive in view of the efficient rescue of sel-12 mutants by expression of HOP-1. There is a surprising amount of divergence between HOP-1 and the other presenilins in the eight transmembrane domains. HOP-1 is different from the human presenilins even in transmembrane domains that are highly conserved between SEL-12 and the human presenilins (compare, for example, TM1 or TM5 in the four proteins; FIG. 1). In general, though, the substitutions appear to be fairly conservative, preserving the hydrophobic character of the transmembrane domains.

SEL-12, PS1 and PS2 have two additional hydrophobic regions that do not span the membrane (8, 9) (see FIG. 3). The C-terminal hydrophobic region is strikingly conserved in sequence and hydrophobicity in HOP-1 as well. However, the internal hydrophobic region of the cytosolic loop of SEL-12 is not appreciably hydrophobic in HOP-1 (see FIG. 3). Nevertheless, there is a notable region of conservation in the cytosolic loop (SEL-12 T232 through S259 and HOP-1 T188 through S215). These observations suggest that, rather than mediating an association with the membrane, this segment may mediate a protein-protein or other molecular interaction necessary for presenilin function (9). It is curious that there is a splice junction conserved in HOP-1, SEL-12, and PS1 just at the end of the conserved region (HOP-1 S215) (there are no available genomic sequence data for PS2).

Functional Redundancy of hop-1 and sel-12.

RNA-mediated interference is a method for reducing endogenous gene activity in C. elegans (22, 23). By using RNA-mediated interference to reduce hop-1 activity, we have found evidence for functional redundancy of hop-1 and sel-12. When hop-1 activity is reduced in a sel-12 mutant background, we observed phenotypes characteristic of glp-1 and lin-12 single mutants, and lin-12 glp-1 double mutants. These results suggest that hop-1, like sel-12 (6), facilitates lin-12 and glp-1 signalling.

The fact that we see hop-1 RNA-mediated interference phenotypes only when sel-12 activity is reduced suggests that hop-1 and sel-12 are functionally redundant. The simplest interpretation of this apparent functional redundancy is that in some cases HOP-1 and SEL-12 may be expressed and may function within the same cells. The cells in which HOP-1 and SEL-12 expression and function overlap might include at least some of the cells undergoing lin-12- and glp-1-mediated cell-cell interactions, so that reducing both hop-1 and sel-12m activity cause characteristic cell fate transformations. Although we have thus far been unable to determine the expression pattern of hop-1 directly, apparently because it is not highly expressed, we note that sel-12 is expressed in many cells and cell types during development (7) and appears to facilitate lin-12 signalling within the same cell (6).

While hop-1 and sel-12 appear to be functionally redundant, we cannot conclude from our experiments that hop-1 does not have any unique roles, since the RNA-mediated interference method may not completely eliminate hop-1 gene activity in a wild-type genetic background. Nevertheless, it is possible that conventional hop-1 null alleles may not cause a significant visible phenotype. However, we expect that hop-1 (−); sel-12(−) double mutants would display highly penetrant phenotypes associated with reducing lin-12 and/or glp-1 activity, and possibly additional defects as well.

Conventional hop-1(−) alleles may therefore be generated as synthetic lethal mutations in a sel-12(−) background. Aternatively, conventional hop-1(−) mutations may be generated by reverse genetic methods that are now standard for C. elegans (32).

Genetic analysis suggests that the hop-1 and sel-12 presenilins facilitate lin-12 and glp-1 activity (ref. 6; this work). Furthermore, targeted disruption of the mouse PS1 gene causes striking phenotypes associated with reduced Notch activity (28, 29). While presenilins may be involved in other processes as well, these observations suggest that there is an intimate relationship between presenilin activity and Notch activity. Understanding the molecular basis for this relationship is an important goal that will be facilitated by further genetic analysis of sel-12 and hop-1, and of suppressors of mutant phenotypes associated with sel-12 and hop-1, in C. elegans.

References

1. Schellenberg, G. D. (1995) *Proc. Natl. Acad. Sci. (USA)* 92, 8552–8559.

2. Levy-Lahad, E., Wijsman, E. M., Nemens, E., Andereson, L., Goddard, K. A., Beber, J. L., Bird, T. D. & Schellenberg, G. D. (1995) *Science* 269, 970–973.
3. Rogaev, E. I., Sherrington, R., Rogaeva, E. A., Levesque, G., Ideda, M., Liang, Y., Chi, H., Lin, C., Holman, K., Tsuda, T., Mar, L., Sorbi, S., Nacmias, B., Piacentini, S., Amaducci, L., Chumakov, I., Cohen, D., Lannfelt, L., Fraser, P. E., Rommens, J. M. & St. George-Hyslop, P. H. (1995) *Nature* 376, 775–778.
4. Sherrington, R., Rogaev, E. I., Liang, Y., Rogaeva, E. A., Levesque, G., Ikeda, M., Chi, H., Lin, C., Li, G., Holman, K., Tsuda, T., Mar, L., Foncin, J. -F., Bruni, A. C., Montesi, M. P., Sorbi, S., Rainero, I., Pinessi, L., Nee, L., Chumakov, I., Pollen, D., Brookes, A., Sanseau, P., Polinsky, R. J., Wasco, W., Da Silva, H. A. R., Haines, J. L., Pericak-Vance, M. A., Tanzi, R. E., Roses, A. D., Fraser, P. E., Rommens, J. M. & St. George-Hyslop, P. H. (1995) *Nature* 375, 754–760.
5. Kovacs, D. M., Fausett, H. J., Page, K. J., Kim, T. -W., Moir, R. D., Merriam, D. E., Hollister, R. D., Hallmark, O. G., Mancini, R., Felsenstein, K. M., Hyman, B. T., Tanzi, R. E. & Wasco, W. (1996) *Nature Medicine* 2, 224–229.
6. Levitan, D. & Greenwald, I. (1995) *Nature* 377, 351–354.
7. Levitan, D., Doyle, T. G., Brousseau, D., Lee, M. K., Thinakaran, G., Slunt, H. H., Sisodia, S. S. & Greenwald, I. (1996) *Proc. Natl. Acad. Sci. (USA)* 93, 14940–14944.
8. Doan, A., Thinakaran, G., Borchelt, D. R., Slunt, H. H., Ratovitsky, T., Podlisny, M., Selkoe, D. J., Seeger, M., Gandy, S. E., Price, D. L. & Sisodia, S. S. (1996) *Neuron* 17.
9. Li, X. & Greenwald, I. (1996) *Neuron* 17, 1015–1021.
10. Thinakaran, G., Borchelt, D. R., Lee, M. K., Slunt, H. H., Spitzer, L., Kim, G., Ratovitsky, T., Davenport, F., Nordstedt, C., Seeger, M., Hardy, J., Levey, A. I., Gandy, S. E., Jenkins, N. A., Copeland, N. G., Price, D. L., & Sisodia, S. S. (1996) *Neuron* 17, 181–190.
11. Waterston, R. H., Sulston, J. E. & Coulson, A. R. (1997) in *C. elegans* II Riddle, D. L., Blumenthal, T., Meyer, B. J. & Priess, J. R., Eds. (Cold Spring Harbor Laboratory Press, pp. 23–46.
12. Edgley, M. L., Turner, C. A. & Riddle, D. L. (1997) in *C. elegans* II Riddle, D. L., Blumenthal, T., Meyer, B. J. & Priess, J. R., Eds. (Cold Spring Harbor Laboratory Press, pp. 1059–1062.
13. Brenner, S. (1974) *Genetics* 77, 71–94.
14. Barstead, R. J. & Waterston, R. H. (1989) *J. Biol. Chem.* 264, 10177–10185.
15. Krause, M. & Hirsh, D. (1987) *Cell* 49, 753–761.
16. Huang, X. -Y. & Hirsh, D. (1989) *Proc. Natl. Acad. Sci. USA* 86, 8640–8644.
17. Fire, A., Harrison, S. W. & Dixon, D. (1990) *Gene* 93, 189–198.
18. Mello, C. C., Kramer, J. M., Stinchcomb, D. T. & Ambros, V. A. (1991) *EMBO Journal* 10, 3959–3970.
19. Fire, A. (1993) *Genet. Anal. Tech. Appl.* 151–158.
20. Silhavy, T. J. & Beckwith, J. R. (1985) *Microbiol. Rev.* 49, 398–418.
21. Froshauer, S., Green, G. N., Boyd, D., McGovern, K. & Beckwith, J. (1988) *J. Mol. Biol.* 200, 501–511.
22. Guo, S. & Kemphues, K. J. (1995) *Cell* 81, 611–620.
23. Rocheleau, C., Downs, W. D., Lin, R., Wittmann, C., Bei, Y., Cha, Y. -H., Ali, M., Priess, J. R. & Mello, C. C. (1997) *Cell* 90, 707–716.
24. Greenwald, I. S., Sternberg, P. W. & Horvitz, H. R. (1983) *Cell* 34, 435–444.
25. Austin, J. & Kimble, J. (1987) *Cell* 51, 589–599.
26. Priess, J. R., Schnabel, H. & Schnabel, R. (1987) *Cell* 51, 601–611.
27. Lambie, E. & Kimble, J. (1991) *Development* 112, 231–240.
28. Shen, J., Bronson, R. T., Chen, D. F., Xia, W., Selkoe, D. J. & Tonegawa, S. (1997) *Cell* 89, 629–639.
29. Wong, P. C., Zheng, H., Chen, H., Becher, M. W., Sirinathsinghji, D. J. S., Trumbauer, M. W., Chen, H. Y., Price, D. L., Van der Ploeg, L. H. T. & Sisodia, S. S. (1997) *Nature* 387, 288–292.
30. Devereux, J., Haeberli, P. & Smithies, O. (1984) *Nucl. Acids Res.* 12, 387–395.
31. Kyte, J. & Doolittle, R. (1982) *J. Mol. Biol.* 157, 105–132.
32. Yandell, M. D., Edgar, L. G. and Wood, W. B. (1994) Proc. Natl. Acad. Sci. (USA) 91:1381–1385.

What is claimed is:

1. An isolated nucleic acid molecule encoding a HOP-1 comprising the nucleotide sequence set forth in SEQ ID NO:8.

2. The isolated nucleic acid molecule of claim 1, wherein the molecule is a DNA, cDNA, or RNA.

3. An isolated nucleic acid molecule of claim 1 operatively linked to a promoter of DNA transcription.

4. A vector which comprises the isolated nucleic acid molecule of claim 3.

5. The vector of claim 4, wherein the vector is a plasmid.

6. A host vector system for the production of a HOP-1 which comprises the vector of claim 5 and a suitable host.

7. The host vector system of claim 6, wherein the suitable host is a bacterial cell, insect cell, plant or animal cell.

* * * * *

SEQUENCE LISTING

<160> NUMBER OF SEQ ID NOS: 8

<210> SEQ ID NO 1
<211> LENGTH: 28
<212> TYPE: DNA
<213> ORGANISM: hop-1 cDNA

<400> SEQUENCE: 1
cgggatcctt tgcatgttgt tcgtcgcg                                28

<210> SEQ ID NO 2
<211> LENGTH: 26
<212> TYPE: DNA
<213> ORGANISM: hop-1 cDNA

<400> SEQUENCE: 2
cgggatccaa attagctgtg aggtgc                                  26

<210> SEQ ID NO 3
<211> LENGTH: 37

-continued

```
<212> TYPE: DNA
<213> ORGANISM: hop-1 cDNA

<400> SEQUENCE: 3
ggccacgcgt cgactagtac ttttttttt tttttt                               37

<210> SEQ ID NO 4
<211> LENGTH: 358
<212> TYPE: PRT
<213> ORGANISM: HOP-1

<400> SEQUENCE: 4
```

Met Pro Arg Thr Lys Arg Val Tyr Ser Gly Lys Thr Ile Thr Gly Val
 1               5                  10                  15

Leu Tyr Pro Val Ala Ile Cys Met Leu Phe Val Ala Ile Asn Val Lys
                20                  25                  30

Leu Ser Gln Pro Glu Gln Glu Gln Ser Lys Val Val Tyr Gly Leu
            35                  40                  45

Phe His Ser Tyr Asp Thr Ala Asp Ser Gly Thr Ile Thr Leu Tyr Leu
        50                  55                  60

Ile Gly Phe Leu Ile Leu Thr Thr Ser Leu Gly Val Phe Cys Tyr Gln
 65                 70                  75                  80

Met Lys Phe Tyr Lys Ala Ile Lys Val Tyr Val Leu Ala Asn Ser Ile
                85                  90                  95

Gly Ile Leu Leu Val Tyr Ser Val Phe His Phe Gln Arg Ile Ala Glu
            100                 105                 110

Ala Gln Ser Ile Pro Val Ser Val Pro Thr Phe Phe Leu Ile Leu
            115                 120                 125

Gln Phe Gly Gly Leu Gly Ile Thr Cys Leu His Trp Lys Ser His Arg
    130                 135                 140

Arg Leu His Gln Phe Tyr Leu Ile Met Leu Ala Gly Leu Thr Ala Ile
145                 150                 155                 160

Phe Ile Leu Asn Ile Leu Pro Asp Trp Thr Val Trp Met Ala Leu Thr
                165                 170                 175

Ala Ile Ser Phe Trp Asp Ile Val Ala Val Leu Thr Pro Cys Gly Pro
            180                 185                 190

Leu Lys Met Leu Val Glu Thr Ala Asn Arg Arg Gly Asp Asp Lys Phe
        195                 200                 205

Pro Ala Ile Leu Tyr Asn Ser Ser Tyr Val Asn Glu Val Asp Ser
    210                 215                 220

Pro Asp Thr Thr Arg Ser Asn Ser Thr Pro Leu Thr Glu Phe Asn Asn
225                 230                 235                 240

Ser Ser Ser Ser Arg Leu Leu Glu Ser Asp Ser Leu Leu Arg Pro Pro
                245                 250                 255

Val Ile Pro Arg Gln Ile Arg Glu Val Arg Glu Val Glu Gly Thr Ile
            260                 265                 270

Arg Leu Gly Met Gly Asp Phe Val Phe Tyr Ser Leu Met Leu Gly Asn
        275                 280                 285

Thr Val Gln Thr Cys Pro Leu Pro Thr Val Val Ala Cys Phe Val Ser
    290                 295                 300

Asn Leu Val Gly Leu Thr Ile Thr Leu Pro Ile Val Thr Leu Ser Gln
305                 310                 315                 320

Thr Ala Leu Pro Ala Leu Pro Phe Pro Leu Ala Ile Ala Ala Ile Phe
                325                 330                 335

Tyr Phe Ser Ser His Ile Ala Leu Thr Pro Phe Thr Asp Leu Cys Thr

Ser Gln Leu Ile Leu Ile
        355

<210> SEQ ID NO 5
<211> LENGTH: 445
<212> TYPE: PRT
<213> ORGANISM: SEL-12

<400> SEQUENCE: 5

Met Pro Ser Thr Arg Arg Gln Gln Glu Gly Gly Gly Ala Asp Ala Glu
 1               5                  10                  15

Thr His Thr Val Tyr Gly Thr Asn Leu Ile Thr Asn Arg Asn Ser Gln
            20                  25                  30

Glu Asp Glu Asn Val Val Glu Glu Ala Glu Leu Lys Tyr Gly Ala Ser
        35                  40                  45

His Val Ile His Leu Glu Phe Val Pro Val Ser Leu Cys Met Ala Leu
    50                  55                  60

Val Val Phe Thr Met Asn Thr Ile Thr Phe Tyr Ser Gln Asn Asn Gly
65                  70                  75                  80

Arg His Leu Leu Tyr Thr Pro Phe Val Arg Glu Thr Asp Ser Ile Val
                85                  90                  95

Glu Lys Gly Leu Met Ser Leu Gly Asn Ala Leu Val Met Leu Cys Val
            100                 105                 110

Val Val Leu Met Thr Val Leu Leu Ile Val Phe Tyr Lys Tyr Lys Phe
        115                 120                 125

Tyr Lys Leu Ile His Gly Trp Leu Ile Val Ser Ser Phe Leu Leu Leu
130                 135                 140

Phe Leu Phe Thr Thr Ile Tyr Val Gln Glu Val Leu Lys Ser Phe Asp
145                 150                 155                 160

Val Ser Pro Ser Ala Leu Leu Val Leu Phe Gly Leu Gly Asn Tyr Gly
                165                 170                 175

Val Leu Gly Met Met Cys Ile His Trp Lys Gly Pro Leu Arg Leu Gln
            180                 185                 190

Gln Phe Tyr Leu Ile Thr Met Ser Ala Leu Met Ala Leu Val Phe Ile
        195                 200                 205

Lys Tyr Leu Pro Glu Trp Thr Val Trp Phe Val Leu Phe Val Ile Ser
210                 215                 220

Val Trp Asp Leu Val Ala Val Leu Thr Pro Lys Gly Pro Leu Arg Tyr
225                 230                 235                 240

Leu Val Glu Thr Ala Gln Glu Arg Asn Glu Pro Ile Phe Pro Ala Leu
                245                 250                 255

Ile Tyr Ser Ser Gly Val Ile Tyr Pro Tyr Val Leu Val Thr Ala Val
            260                 265                 270

Glu Asn Thr Thr Asp Pro Arg Glu Pro Thr Ser Ser Asp Ser Asn Thr
        275                 280                 285

Ser Thr Ala Phe Pro Gly Glu Ala Ser Cys Ser Ser Glu Thr Pro Lys
290                 295                 300

Arg Pro Lys Val Lys Arg Ile Pro Gln Lys Val Gln Ile Glu Ser Asn
305                 310                 315                 320

Thr Thr Ala Ser Thr Thr Gln Asn Ser Gly Val Arg Val Glu Arg Glu
                325                 330                 335

Leu Ala Ala Glu Arg Pro Thr Val Gln Asp Ala Asn Phe His Arg His
            340                 345                 350

```
Glu Glu Glu Glu Arg Gly Val Lys Leu Gly Leu Gly Asp Phe Ile Phe
            355                 360                 365

Tyr Ser Val Leu Leu Gly Lys Ala Ser Ser Tyr Phe Asp Trp Asn Thr
        370                 375                 380

Thr Ile Ala Cys Tyr Val Ala Ile Leu Ile Gly Leu Cys Phe Thr Leu
385                 390                 395                 400

Val Leu Leu Ala Val Phe Lys Arg Ala Leu Pro Ala Leu Pro Ile Ser
                405                 410                 415

Ile Phe Ser Gly Leu Ile Phe Tyr Phe Cys Thr Arg Trp Ile Ile Thr
            420                 425                 430

Pro Phe Val Thr Gln Val Ser Gln Lys Cys Leu Leu Tyr
            435                 440                 445

<210> SEQ ID NO 6
<211> LENGTH: 463
<212> TYPE: PRT
<213> ORGANISM: PS1

<400> SEQUENCE: 6

Met Thr Glu Leu Pro Ala Pro Leu Ser Tyr Phe Gln Asn Ala Gln Met
  1               5                  10                  15

Ser Glu Asp Asn His Leu Ser Asn Thr Asn Asp Asn Arg Glu Arg Gln
             20                  25                  30

Glu His Asn Asp Arg Arg Ser Leu Gly His Pro Glu Pro Leu Ser Asn
         35                  40                  45

Gly Arg Pro Gln Gly Asn Ser Arg Gln Val Val Glu Gln Asp Glu Glu
     50                  55                  60

Glu Asp Glu Glu Leu Thr Leu Lys Tyr Gly Ala Lys His Val Ile Met
 65                  70                  75                  80

Leu Phe Val Pro Val Thr Leu Cys Met Val Val Val Val Ala Thr Ile
                 85                  90                  95

Lys Ser Val Ser Phe Tyr Thr Arg Lys Asp Gly Gln Leu Ile Tyr Thr
            100                 105                 110

Pro Phe Thr Glu Asp Thr Glu Thr Val Gly Gln Arg Ala Leu His Ser
        115                 120                 125

Ile Leu Asn Ala Ala Ile Met Ile Ser Val Ile Val Val Met Thr Ile
130                 135                 140

Leu Leu Val Val Leu Tyr Lys Tyr Arg Cys Tyr Lys Val Ile His Ala
145                 150                 155                 160

Trp Leu Ile Ile Ser Ser Leu Leu Leu Leu Phe Phe Ser Phe Ile
                165                 170                 175

Tyr Leu Gly Glu Val Phe Lys Thr Thr Asn Val Ala Val Asp Tyr Ile
            180                 185                 190

Thr Val Ala Leu Leu Ile Trp Asn Leu Gly Val Val Gly Met Ile Ser
        195                 200                 205

Ile His Trp Lys Gly Pro Leu Arg Leu Gln Gln Ala Tyr Leu Ile Met
    210                 215                 220

Ile Ser Ala Leu Met Ala Leu Val Phe Ile Lys Tyr Leu Pro Glu Trp
225                 230                 235                 240

Thr Ala Trp Leu Ile Leu Ala Val Ile Ser Val Tyr Asp Leu Val Ala
                245                 250                 255

Val Leu Cys Pro Lys Gly Pro Leu Arg Met Leu Val Glu Thr Ala Gln
            260                 265                 270

Glu Arg Asn Glu Thr Leu Phe Pro Ala Leu Ile Tyr Ser Ser Thr Met
        275                 280                 285
```

-continued

```
Val Trp Leu Val Asn Met Ala Glu Gly Asp Pro Glu Ala Gln Arg Arg
    290                 295                 300

Val Ser Lys Asn Ser Lys Tyr Asn Ala Glu Ser Thr Glu Arg Glu Ser
305                 310                 315                 320

Gln Asp Thr Val Ala Glu Asn Asp Asp Gly Gly Phe Ser Glu Glu Trp
                325                 330                 335

Glu Ala Gln Arg Asp Ser His Leu Gly Pro His Arg Ser Thr Pro Glu
            340                 345                 350

Ser Arg Ala Ala Val Gln Glu Leu Ser Ser Ser Ile Leu Ala Gly Glu
        355                 360                 365

Asp Pro Glu Glu Arg Gly Val Lys Leu Gly Leu Gly Asp Phe Ile Phe
370                 375                 380

Tyr Ser Val Leu Val Gly Lys Ala Ser Ala Thr Ala Ser Gly Asp Trp
385                 390                 395                 400

Asn Thr Thr Ile Ala Cys Phe Val Ala Ile Leu Ile Gly Leu Cys Leu
                405                 410                 415

Thr Leu Leu Leu Leu Ala Ile Phe Lys Lys Ala Leu Pro Ala Leu Pro
            420                 425                 430

Ile Ser Ile Thr Phe Gly Leu Val Phe Tyr Phe Ala Thr Asp Tyr Leu
        435                 440                 445

Val Gln Pro Phe Met Asp Gln Leu Ala Phe His Gln Phe Tyr Ile
    450                 455                 460

<210> SEQ ID NO 7
<211> LENGTH: 448
<212> TYPE: PRT
<213> ORGANISM: PS2

<400> SEQUENCE: 7

Met Leu Thr Phe Met Ala Ser Asp Ser Glu Glu Glu Val Cys Asp Glu
  1               5                  10                  15

Arg Thr Ser Leu Met Ser Ala Glu Ser Pro Thr Pro Arg Ser Cys Gln
                20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Asp Pro Asp Arg Tyr Val
    50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Val Ala Thr Ile Lys Ser Val Arg Phe Tyr
            100                 105                 110

Thr Glu Lys Asn Gly Gln Leu Ile Tyr Thr Pro Phe Thr Glu Asp Thr
        115                 120                 125

Pro Ser Val Gly Gln Arg Leu Leu Asn Ser Val Leu Asn Thr Leu Ile
    130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Leu Thr Val
```

```
                195                 200                 205
Trp Asn Phe Gly Ala Val Gly Met Val Cys Ile His Trp Lys Gly Pro
    210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
                260                 265                 270

Pro Leu Arg Met Leu Val Glu Thr Ala Gln Glu Arg Asn Glu Pro Ile
                275                 280                 285

Phe Pro Ala Leu Ile Tyr Ser Ser Ala Met Val Trp Thr Val Gly Met
                290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335

Pro Glu Val Phe Glu Pro Pro Leu Thr Gly Tyr Pro Gly Glu Glu Leu
                340                 345                 350

Glu Glu Glu Glu Glu Arg Gly Val Lys Leu Gly Leu Gly Asp Phe Ile
                355                 360                 365

Phe Tyr Ser Val Leu Val Gly Lys Ala Ala Ala Thr Gly Ser Gly Asp
                370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415

Pro Ile Ser Ile Thr Phe Gly Leu Ile Phe Tyr Phe Ser Thr Asp Asn
                420                 425                 430

Leu Val Arg Pro Phe Met Asp Thr Leu Ala Ser His Gln Leu Tyr Ile
                435                 440                 445
```

<210> SEQ ID NO 8
<211> LENGTH: 1074
<212> TYPE: DNA
<213> ORGANISM: HOP-1

<400> SEQUENCE: 8

```
atgccaagaa caaaaagagt gtactccggg aaaaccataa caggagttct ctatcctgtt      60
gcaatttgca tgttgttcgt cgcgataaat gtgaaactca gccagccaga acaacaagaa     120
caatctaaag tagtatacgg actgttccat tcatacgata ccgcggatag cgggacaatc     180
actttgtatt tgattggatt tttgattttg acgactagtt tgggagtttt ttgttatcag     240
atgaagtttt ataaggccat aaaagtatac gtattagcca acagcattgg aattctgctg     300
gtttactcag ttttccattt ccaaagaata gctgaagccc aatcaattcc agtatctgta     360
ccaacatttt tcttccttat tctccaattc ggtggtcttg aataacatg tctccactgg      420
aaatcccatc gacgacttca tcaatttat cttattatgc tcgcaggtct aactgcaatt      480
tttattctca atattcttcc cgactggact gtttggatgg cattaacagc gatttcattt     540
tgggatattg ttgctgttct gacaccgtgt ggaccattaa aaatgctcgt ggaaactgcg     600
aatcgacgcg gagacgacaa atttccagct attttataca attcaagttc atacgtgaat     660
gaagtggatt cccctgacac aacacgatca aacagtaccc cgctaactga attcaacaat     720
```

| | | | | | |
|---|---|---|---|---|---|
| tcatcgagtt | caaggctttt | ggaatctgat | tcacttttga | ggcctccagt | gattcccaga | 780 |
| cagattagag | aagtacgaga | agttgaagga | acaattcggt | taggaatggg | agattttgta | 840 |
| ttttattcac | tgatgttggg | aaatactgtt | caaacgtgcc | cacttccaac | tgtcgtcgcg | 900 |
| tgcttcgtat | ccaatcttgt | tggtttgaca | attactctgc | caattgtcac | attatctcaa | 960 |
| actgcacttc | cagcattgcc | gttcccgttg | gcaattgcag | caatattcta | cttctcctcc | 1020 |
| catatcgcat | taaccccatt | caccgatctg | tgcacctcac | agctaattt | aatt | 1074 |